(12) United States Patent
Delangle et al.

(10) Patent No.: US 9,856,294 B2
(45) Date of Patent: Jan. 2, 2018

(54) CYCLODECAPEPTIDE COMPOUNDS FOR USE AS DRUGS

(75) Inventors: Pascale Delangle, Voiron (FR); Anaïs Pujol, Andernos les Bains (FR); Pascal Dumy, Grenoble (FR); Olivier Renaudet, St Pierre D'Allevard (FR); Michel Ferrand, Reaumont (FR)

(73) Assignees: Commissariat A L'Energie Atomique Et Aux Energies Alternatives, Paris (FR); Universite Joseph Fourier, Grenoble (FR)

( * ) Notice: Subject to any disclaimer, the term of this patent is extended or adjusted under 35 U.S.C. 154(b) by 190 days.

(21) Appl. No.: 13/698,450

(22) PCT Filed: May 17, 2011

(86) PCT No.: PCT/IB2011/052162
§ 371 (c)(1),
(2), (4) Date: Jun. 7, 2013

(87) PCT Pub. No.: WO2011/145055
PCT Pub. Date: Nov. 24, 2011

(65) Prior Publication Data
US 2013/0251639 A1    Sep. 26, 2013

(30) Foreign Application Priority Data
May 17, 2010  (FR) ..................... 10 02062

(51) Int. Cl.
*C07K 9/00* (2006.01)
*C07K 7/64* (2006.01)
*A61K 49/00* (2006.01)

(52) U.S. Cl.
CPC .......... *C07K 9/006* (2013.01); *A61K 49/0056* (2013.01); *C07K 7/64* (2013.01)

(58) Field of Classification Search
CPC ............................ C07K 9/006; A61K 49/0056
See application file for complete search history.

(56) References Cited

U.S. PATENT DOCUMENTS

2006/0173160 A1* 8/2006 Dumy ............... C07K 9/006
                                                    530/317
2009/0221449 A1   9/2009 Defrancq et al.

FOREIGN PATENT DOCUMENTS

WO    WO-2007/096517 A1    8/2007

OTHER PUBLICATIONS

Peng Z. Can. J Chem 77:1394-1404, published 1999 (in IDS of Jul. 7, 2013).*

Pujol A et al "Hepatocyte Targeting and Intracellular Copper Chelation by a Thiol-Containing Glycocyclopeptide" J. Am. Chem. Soc. 133:286-296. Published online Dec. 14, 2010.*
Xu Q et al "A useful bicyclic topological decapeptide template for solution-phase combinatorial synthesis of tetrapodal libraries" Tetrahedron Letters 42:7261-7263. Published 2001.*
Rousselot-Pailley et al. "Model Peptides Based on the Binding Loop of the Copper Metallochaperone Atx1: Selectivity of the Consensus Sequence MxCxxC for Metal Ions Hg (II), Cu(I), Cd(II), Pb(II), and Zn(II)". Inorgan. Chem. 45:5510-5520. Published 2006.*
Wu et al. "Amino Acid Influence on Copper Binding to Peptides: Cysteine Versus Arginine" J. Am. Soc. Mass. Spectrom. 21:522-533. Published Jan. 11, 2010.*
Renaudet O and Dumy P "A Fully Solid-Phase Synthesis of Biotinylated Glycoclusters" Open Glycoscience 1:1-7. Published 2008.*
Andersen, O.; "*Principles and Recent Developments in Chelation Treatment of Metal Intoxication;*" Chemical Reviews, vol. 99, No. 9; pp. 2683-2710; dated Aug. 1999.
Berthelot, T., et al.; "*New Trends in Molecular Imaging of Tumor Angiogenesis;*" Anti-Cancer Agents in Medicinal Chemistry, vol. 8, No. 5; pp. 497-522; dated Jun. 2008; abstract retrieved on Jun. 6, 2013 from <http://www.ingentaconnect.com/content/ben/acamc/2008/00000008/00000005/art00006>.
Boturyn, D. et al.; "*RAFT Nano-constructs: surfing to biological applications;*" Journal of Peptide Science, vol. 14, No. 2; pp. 224-240; dated Feb. 2008.
Brewer, G. J.; "*Anticopper therapy against cancer and diseases of inflammation and fibrosis;*" Drug Discovery Today, vol. 10, No. 16; pp. 1103-1109; dated Aug. 2005; abstract retrieved on Jun. 6, 2013 from <http://www.ncbi.nlm.nih.gov/pubmed/16182195>.
Brewer, G. J., et al.; "*Wilson's Disease: clinical management and therapy;*" Journal of Hepatology, vol. 42, No. 1; pp. S13-S21; dated Apr. 2005; retrieved on Jun. 6, 2013 from <http://download.journals.elsevierhealth.com/pdfs/journals/0168-8278/PIIS0168827804005318.pdf>.
Decaens, C., et al.; "*Establishment of hepatic cell polarity in the rat hepatoma-human fibrolast hybrid WIF-B9. A biphasic phenomenon going from a simple epithelial polarized phenotype to an hepatic polarized one;*" Journal of Cell Science, vol. 109, No. 6; pp. 1623-1635; dated Jun. 1996; retrieved on Jun. 6, 2013 from <http://jcs.biologists.org/content/109/6/1623.full.pdf+html>.

(Continued)

*Primary Examiner* — Christina Bradley
*Assistant Examiner* — Zachary K Miknis
(74) *Attorney, Agent, or Firm* — Alston & Bird LLP

(57) ABSTRACT

The invention relates to novel cyclodecapeptide compounds having formula (I) for use as drugs and, more specifically, for use in the diagnosis, prevention and/or treatment of neurodegenerative diseases, such as Wilson's disease and Alzheimer's disease, and for use in the diagnosis, prevention and/or treatment of poisoning with metal ions, such as copper and mercury ions. The invention also relates to pharmaceutical compositions comprising at least one compound having formula (I) as an active principle.

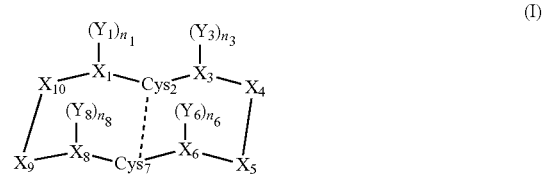

(I)

12 Claims, 7 Drawing Sheets

(56) References Cited

OTHER PUBLICATIONS

Fouillard, S., et al.; "*1-Ethoxyethylidene, a New Group for the Stepwise SPPS of Aminooxyacetic Acid Containing Peptides;*" Journal of Organic Chemistry, vol. 73, No. 3; pp. 983-991; dated Feb. 2008; retrieved on Jun. 6, 2013 from <http://www.researchgate.net/publication/5677291_1-Ethoxyethylidene_a_new_group_for_the_stepwise_SPPS_of_aminooxyacetic_acid_containing_peptides>.

Gaggelli, E., et al.; "*Copper Homeostasis and Neurodegenerative Disorders (Alzheimer's, Prion, and Parkinson's Diseases and Amyotrophic Lateral Sclerosis);*" Chemical Reviews; vol. 106, No. 6; pp. 1995-2044; dated Jun. 2006; retrieved on Jun. 6, 2013 from <gaodengwj.chem.bnu.edu.cn/Copper%20Homeostasis.pdf>.

Guo, Y., et al.; "*$NH_2$-terminal signals in ATP7B Cu-ATPase mediate its Cu-dependence anterograde traffic in polarized hepatic cells;*" Am. J. Physiol. Gastrointestinal Liver. Physiol., vol. 289, No. 5; pp. G904-G916; dated Nov. 2005; retrieved on Jun. 6, 2013 from <http://ajpgi.physiology.org/content/289/5/G904.full.pdf+html>.

Hefter, M., et al.; "*A general method for the determination of copper(I) equilibria in aqueous solution;*" Journal of the Chemical Society, Chemical Communications., vol. 1993, No. 2; pp. 1704-1706; dated 1993; abstract retrieved on Jun. 6, 2013 from <http://pubs.rsc.org/en/content/articlelanding/1993/c3/c39930001704>.

Hernandez et al.; "*ATP7B Copper-Regulated Traffic and Association With the Tight Junctions: Copper Excretion Into the Bile;*" Gastroenterology, vol. 134, No. 4; pp. 1215-1223; dated Apr. 2008; retrieved on Jun. 6, 2013 from <http://download.journals.elsevierhealth.com/pdfs/journals/0016-5085/PIIS0016508508001170.pdf>.

McNamara, G., et al.; "*Spectral Imaging Microscopy Web Sites and Data;*" Cytometry Part A, vol. 69A, No. 8; pp. 863-871; dated Aug. 2006; retrieved on Jun. 6, 2013 from <http://onlinelibrary.wiley.com/doi/10.1002/cyto.a.20304/pdf>.

Peng, X., et al.; "*How to induce non-polarized cells of hepatic origin to express typical hepatocyte polarity: generation of new highly polarized cell models with developed and functional bile canaliculi;*" Cell and Tissue Research, vol. 323, No. 2; pp. 233-243; dated Feb. 2006; abstract retrieved on Jun. 6, 2013 from <http://link.springer.com/article/10.1007/s00441-005-0067-2>.

Peng, Z.; "*NMR conformational analysis on cyclic decapeptide template molecule;*" Canadian Journal of Chemistry, vol. 77, No. 8; pp. 1394-1404; dated 1999.

Portney, N. G., et al.; "*Nano-oncology: drug delivery, imagining, and sensing;*" Analytical and Bioanalytical Chemistry, vol. 384, No. 3; pp. 620-630; dated Feb. 2006; abstract retrieved on Jun. 6, 2013 from <http://link.springer.com/article/10.1007/s00216-005-0247-7>.

Renaudet et al.; "*On-bead synthesis and binding assay of chemoselectively template-assembled multivalent neoglycopeptides;*" Organic & Bimolecular Chemistry, vol. 4, No. 13; pp. 2628-2636; dated 2006; abstract retrieved on Jun. 6, 2013 from <http://pubs.rsc.org/en/content/articlelanding/2006/ob/b604391g>.

Riddles, P. W., et al.; "*Reassessment of Ellman's reagent;*" Methods Enzymology, vol. 91, No. 8 pp. 49-60; dated 1983.

Rousselot-Pailley, P., et al.; "*Model Peptide Based on the Binding Loop of the Copper Metallochaperone Atx1: Selectivity of the Consensus Sequence MxCxxC for Metal Ions Hg(II), Cu(I), Cd(II), Pb(II), and Zn(II);*" Inorganic Chemistry, vol. 45, No. 14; pp. 5510-5520; dated Jul. 2006.

Sarkar, B.; "*Treatment of Wilson and Menkes Diseases;*" Chemcal Reviews, vol. 99, No. 9; pp. 2535-2544; dated Aug. 1999.

Sheppard, R.; "*The fluorenylmethoxycarbonyl group in solid phase synthesis;*" Journal of Peptide Science, vol. 9, No. 9; pp. 545-552; dated Sep. 2003; abstract retrieved on Jun. 6, 2013 from <http://onlinelibrary.wiley.com/doi/10.1002/psc.479/abstract>.

Singh, Y., et al.; "*Synthetic Peptide Templates for Molecular Recognition: Recent Advances and Applications;*" ChemBioChem, vol. 7, No. 9; pp. 1298-1314; dated Sep. 2006.

Smith, R. M., et al.; "*NIST Critically Selected Stability Constants of Metal Complexes Database, Version 8.0 for Windows, User's Guide;*" NIST Standard Reference Database 46; dated 2004; retrieved on Jun. 6, 2013 from <http://www.nist.gov/srd/nist46.cfm>.

Xiao, Z., et al.; "*C-Terminal Domain of the Membrane Copper Transporter Ctr1 from Saccharomyces cerevisiae Binds Four Cu(I) Ions as a Cuprous-Thiolate Polynuclear Cluster: Sub-femtomolar Cu(I) Affinity of Three Proteins Involved in Copper Trafficking;*" Journal of the American Chemical Society, vol. 126, No. 10; pp. 3081-3090; dated Mar. 2004; abstract retrieved on Jun. 6, 2013 from <http://pubs.acs.org/doi/abs/10.1021/ja0390350>.

Xu, Q., et al.; "*A useful bicyclic topological decapeptide template for solution-phase combinatorial synthesis of tetrapodal libraries;*" Tetrahedron Letters, vol. 42, No. 41; pp. 7261-7263; dated Oct. 2001.

International Search Report and Written Opinion for Application No. PCT/IB2011/052162; dated Oct. 13, 2011.

Pujol, Anais M., et al.; "*Hepatocyte Targeting and Intracellular Copper Chelation by a Thiol-Containing Glycocyclopeptide;*" J. Am. Chem. Soc., vol. 133, pp. 286-296; 2011.

\* cited by examiner

SEQUENCE LISTING

```
<160> NUMBER OF SEQ ID NOS: 4

<210> SEQ ID NO 1
<211> LENGTH: 10
<212> TYPE: PRT
<213> ORGANISM: artificial sequence
<220> FEATURE:
<223> OTHER INFORMATION: cyclodecapeptide compound of formula I
<220> FEATURE:
<221> NAME/KEY: MISC FEATURE
<222> LOCATION: 1 1
<223> OTHER INFORMATION: X is an amino acid present in its
      dextrorotatory or levorotatory form, and may be substituted with a
      group Y1 selected from COCHNL, COEL or NHEL in which L is a
      biological ligand and E is a spacer arm
```

```
<220> FEATURE:
<221> NAME/KEY: MISC_FEATURE
<222> LOCATION: 2 2
<223> OTHER INFORMATION: this cysteine amino acid may or may not be
      linked by a covalent bond to the cysteine amino acid in position
      7, via their sulfur atoms
<220> FEATURE:
<221> NAME/KEY: MISC_FEATURE
<222> LOCATION: 3 3
<223> OTHER INFORMATION: X is an amino acid present in its
      dextrorotatory or levorotatory form, and may be substituted with a
      group Y3 selected from COCHNL, COEL or NHEL in which L is a
      biological ligand and E is a spacer arm
<220> FEATURE:
<221> NAME/KEY: MISC_FEATURE
<222> LOCATION: 4 5
<223> OTHER INFORMATION: X is an amino acid present in its
      dextrorotatory or levorotatory form
<220> FEATURE:
<221> NAME/KEY: MISC_FEATURE
<222> LOCATION: 4 5
<223> OTHER INFORMATION: X may be substituted with a group selected from
      CO marker, NH marker, CSNH marker, SO2 marker, CH marker, E
      marker, where E is a spacer arm
<220> FEATURE:
<221> NAME/KEY: MISC_FEATURE
<222> LOCATION: 4 5
<223> OTHER INFORMATION: the bond X4 X5 is chosen from the bonds DPro LX
      or LPro DX, in which X and X are amino acids
<220> FEATURE:
<221> NAME/KEY: MISC_FEATURE
<222> LOCATION: 6 6
<223> OTHER INFORMATION: X is an amino acid present in its
      dextrorotatory or levorotatory form, and may be substituted with a
      group Y6 selected from COCHNL, COEL or NHEL in which L is a
      biological ligand and E is a spacer arm
<220> FEATURE:
<221> NAME/KEY: MISC_FEATURE
<222> LOCATION: 7 7
<223> OTHER INFORMATION: this cysteine amino acid may or may not be
      linked by a covalent bond to the cysteine amino acid in position
      2, via their sulfur atoms
<220> FEATURE:
<221> NAME/KEY: MISC_FEATURE
<222> LOCATION: 8 8
<223> OTHER INFORMATION: X is an amino acid present in its
      dextrorotatory or levorotatory form, and may be substituted with a
      group Y8 selected from COCHNL, COEL or NHEL in which L is a
      biological ligand and E is a spacer arm
<220> FEATURE:
<221> NAME/KEY: MISC_FEATURE
<222> LOCATION: 9 10
<223> OTHER INFORMATION: X is an amino acid present in its
      dextrorotatory or levorotatory form
<220> FEATURE:
<221> NAME/KEY: MISC_FEATURE
<222> LOCATION: 9 10
<223> OTHER INFORMATION: X may be substituted with a group selected from
      CO marker, NH marker, CSNH marker, SO2 marker, CH marker,
      E marker, where E is a spacer arm
<220> FEATURE:
<221> NAME/KEY: MISC_FEATURE
<222> LOCATION: 9 10
<223> OTHER INFORMATION: the bond X9 X10 is chosen from the bonds DPro
      LX or LPro DX, in which X and X are amino acids

<400> SEQUENCE: 1

Xaa Cys Xaa Xaa Xaa Xaa Cys Xaa Xaa Xaa
1               5                   10

<210> SEQ ID NO 2
<211> LENGTH: 10
<212> TYPE: PRT
<213> ORGANISM: artificial sequence
<220> FEATURE:
<223> OTHER INFORMATION: cyclodecapeptide compound P1
```

```
<400> SEQUENCE: 2

Arg Cys Ser Pro Gly Ser Cys Trp Pro Gly
1               5                   10

<210> SEQ ID NO 3
<211> LENGTH: 10
<212> TYPE: PRT
<213> ORGANISM: artificial sequence
<220> FEATURE:
<223> OTHER INFORMATION: cyclodecapeptide compound P2

<400> SEQUENCE: 3

Trp Cys Glu Pro Gly Glu Cys Asp Pro Gly
1               5                   10

<210> SEQ ID NO 4
<211> LENGTH: 10
<212> TYPE: PRT
<213> ORGANISM: artificial sequence
<220> FEATURE:
<223> OTHER INFORMATION: cyclodecapeptide compound P3
<220> FEATURE:
<221> NAME/KEY: MISC FEATURE
<222> LOCATION: 1 1
<223> OTHER INFORMATION: this lysine amino acid is substituted with a
      COCHNL group
<220> FEATURE:
<221> NAME/KEY: MISC FEATURE
<222> LOCATION: 2 2
<223> OTHER INFORMATION: this cysteine amino acid is linked by a
      covalent bond to the cysteine amino acid in position 7, via their
      sulfur atoms
<220> FEATURE:
<221> NAME/KEY: MISC FEATURE
<222> LOCATION: 3 3
<223> OTHER INFORMATION: this lysine amino acid is substituted with a
      COCHNL group
<220> FEATURE:
<221> NAME/KEY: MISC FEATURE
<222> LOCATION: 5 5
<223> OTHER INFORMATION: D lysine amino acid, which may be substituted
      with a TRITC group
<220> FEATURE:
<221> NAME/KEY: MISC FEATURE
<222> LOCATION: 6 6
<223> OTHER INFORMATION: this lysine amino acid is substituted with a
      COCHNL group
<220> FEATURE:
<221> NAME/KEY: MISC FEATURE
<222> LOCATION: 7 7
<223> OTHER INFORMATION: this cysteine amino acid is linked by a
      covalent bond to the cysteine amino acid in position 2, via their
      sulfur atoms
<220> FEATURE:
<221> NAME/KEY: MISC FEATURE
<222> LOCATION: 8 8
<223> OTHER INFORMATION: this lysine amino acid is substituted with a
      COCHNL group

<400> SEQUENCE: 4

Lys Cys Lys Pro Lys Lys Cys Lys Pro Gly
1               5                   10
```

CYCLODECAPEPTIDE COMPOUNDS FOR USE AS DRUGS

FIELD

The present invention relates to novel cyclodecapeptide compounds of formula (I) for their use as drugs, and more particularly their use for the diagnosis, prevention and/or treatment of neurodegenerative diseases, such as Wilson's and Alzheimer's diseases, and their use for the diagnosis, prevention and/or treatment of poisoning with metal ions such as copper and mercury ions. Pharmaceutical compositions comprising, as active ingredient, at least one compound of formula (I) also form part of the invention.

BACKGROUND

Diseases linked to disruption of the transport of copper, such as Wilson's disease, lead to an accumulation of copper in the liver, which is the sole organ capable of excreting it. Thus, although copper is an element that is essential for life, it can, in the free state, induce oxidation reactions of the Fenton type and, consequently, prove extremely toxic. More particularly, Wilson's disease is a genetic disease linked to a deficiency of a copper transporter, leading to an accumulation of copper in various regions of the body (up to 20 times the normal levels), which manifests itself by impairment of the liver and of the nervous system. It leads to a disruption of the physiological concentrations of copper in the individual, which manifests itself by severe neurological and hepatic disorders. Psychological disorders may appear with changes in the character, leading to hyperemotivity with high mood lability, depressive syndromes and psychotic states. Wilson's disease is induced by the mutation of the ATP7B gene, which codes for a transmembrane protein of the ATPase type, involved in the transport of copper, allowing the regulation of the concentration of copper, and its excretion in the bile. If the protein is deficient, the metal then accumulates inside the cells. Impairment of the liver precedes, as a general rule, the neurological impairment by a few years. The neurological or psychiatric signs affect nearly 50% of the patients with Wilson's disease. Magnetic resonance imaging (MRI) shows lesions of several brain structures, even in the absence of any clinical sign and the extent thereof appears to correlate with the degree of advancement of the disease. In extremely serious cases of fulminant hepatitis or in essentially hepatic serious impairments, a liver transplant may be envisaged.

Currently, treatments exist which are aimed at eradicating the toxicity of the copper that has accumulated in the body. These treatments must be followed for life, and must never be interrupted. They are based on chelating drugs which reduce the absorption of copper in the body, or which increase the excretion of this metal. The treatments must be subject to periodic monitoring, so as to detect the appearance of undesirable side effects. The existing treatments use various active ingredients, such as:

D-penicillamine (Pen), which increases urinary excretion of copper (G. J. Brewer, DDT, 2005, 10, pp. 1103-1109). D-penicillamine has a recognized efficacy and forms with copper(I) a Cu(I)-Pen complex which has a stability constant of $10^{12}$ (M. Hefter et al., J. C. S., Chem. Commun., 1993, 1704-1706), however it has numerous side effects which tend to cause it to be replaced by other molecules. Moreover, a number of recent articles report a worsening of Wilson's disease with D-penicillamine and suggest restricting its prescription in this indication;

triethylenetetramine (Trien), which is a copper chelator that is often better tolerated than D-penicillamine, and which forms a Cu(II)-Triene complex with copper(II) having a stability constant of $10^{20}$ (R. M. Smith et al., 2001, NIST Critically Selected Stability Constants of Metal Complexes Database, NIST Standard Reference Database 46);

the ammonium tetrathiomolybdate (TTM) anion, taken with food, which binds with the copper ions in the digestive tube, thus preventing their absorption;

zinc activates the production of proteins, the metallothioneins, which will bind the copper in the cells of the intestinal wall (enterocytes), preventing the passage of this ion into the blood stream (B. Sarkar, Chem. Rev., 1999, 99, 2535-2544).

Currently, drugs based on D-penicillamine, whose mechanism of action is still poorly known, are the most widely used. By virtue of its SH functional group, D-penicillamine can:

chelate copper and zinc, but also mercury and lead, and increase their urinary excretion, reduce the disulfide bridges of certain molecules: collagen, elastic fibers, immunoglobulins, and thus modify their biological activity, combine with other sulfur-containing molecules, in particular cysteine, forming disulfide bridges.

It indeed appears that the presence of soft atoms, such as sulfur, allows a more effective chelation of the so-called "soft ion" metal ions such as copper Cu(I) and mercury Hg(II).

Other drugs also exist whose action is comparable to that of D-penicillamine because of the similarity of their pharmacological properties:

pyritinol, which is a symmetrical molecule formed of two parts linked by a disulfide bridge. In the body, pyritinol is cleaved into two molecules, each containing an —SH group. However, pyritinol has been used in the treatment of rheumatoid arthritis with indications and undesirable effects of the same type as those of D-penicillamine, tiopronin, which is used in the long-term treatment of rheumatoid arthritis and of cystine lithiasis.

However, the undesirable effects of D-penicillamine and of drugs having a similar mode of action are fairly high in number:

early cutaneo-mucosal and not very serious: erythema, stomatitis, late cutaneo-mucosal and serious: toxicoderma, pemphigus, dermatomyositis, hematological: thrombopenia, leukopenia, agranulocytosis, hemolytic anemia, justifying hematological monitoring of the patients treated, digestive: ageusia, renal: proteinuria.

Metals are also considered as therapeutic targets of interest for the diagnosis, prevention and/or treatment of neurodegenerative diseases such as Alzheimer's disease, for which the dysregulation of zinc and copper homeostasis plays a critical role. The copper Cu(II) is complexed and reduced to copper Cu(I) by the APP protein and the Aβ peptide, the copper Cu(I) then accumulating in the amyloid plaques with iron and zinc (E. Gaggelli et al., 2006, 106, 1995-2044).

Copper has two stable oxidation states under different conditions: copper Cu(I) having an oxidation state +I, which is stable in a reducing medium, and copper Cu(II) having an oxidation state +II, which is stable in an oxygenated medium. The copper that is present in human cells is mainly copper Cu(I).

Molecules other than D-penicillamine (Pen), may also be used to chelate copper in vivo. They are, for example, 2,3-dimercaptosuccinic acid (DMSA) and 2,3-dimercapto-1-propanesulfonic acid (DMPS) (O. Andersen, Chem. Rev., 1999, 99, 2683-2710), 2,3-dimercaptopropanol (BAL), triethylenetetramine (Trien), the ammonium tetrathiomolybdate (TTM) anion (G. J. Brewer et al., J. Hepatol., 2005, 42, S13-S21) and ethylenediaminetetraacetic acid (EDTA), which correspond to the following semi-structural formulae:

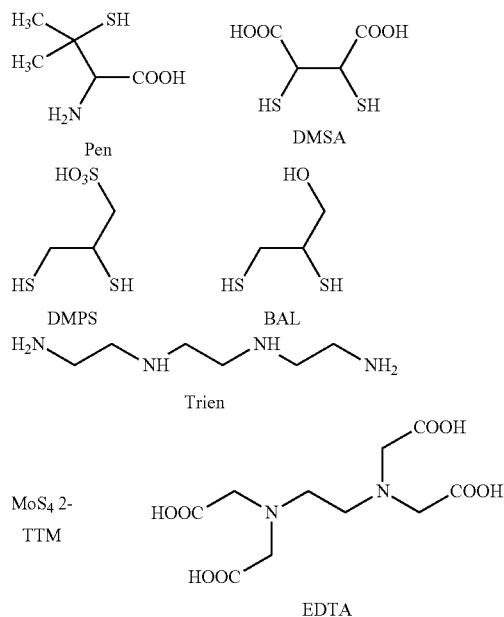

These compounds are known chelating agents for copper Cu(I) and/or copper Cu(II), which block the intestinal absorption of copper. However, these compounds lead to undesirable side effects, and do not allow the treatment of patients for whom the diseases have been detected at an already advanced stage (non-early detection), and for whom there is a large intracellular accumulation of copper (B. Sarkar, Chem. Rev., 1999, 99, 2535-2534; G. J. Brewer et al., J. Hepatol., 2005, 42, S13-S21). Furthermore, some chelating agents, such as EDTA, are very strong chelating agents, which chelate numerous metal ions, and one of the main disadvantages of which is their lack of selectivity.

The apparent complexation constants of some known chelating agents (R. M. Smith et al., 2001, NIST Critically Selected Stability Constants of Metal Complexes Database, NIST Standard Reference Database 46) are reported in table I below:

TABLE I

| Log $K_{app}$ at T = 298 K (at pH = 7.4) | EDTA | Trien | Pen | BAL |
|---|---|---|---|---|
| Ca(II) | 7.8 | — | — | — |
| Cu(I) | — | — | 8.3 | — |
| Cu(II) | 16.0 | 16.0 | — | — |
| Zn(II) | 13.7 | 7.9 | 5.8 | 9.0 |
| Cd(II) | 13.7 | 6.6 | 7.6 | — |
| Hg(II) | 18.7 | 20.6 | 14.9 | 21.2 |
| Pb(II) | 15.2 | 6.3 | 9.2 | — |
| Selectivity Cu/Zn | 2.3 | 8.1 | 2.5 | — |
| Selectivity Hg/Zn | 5 | 12.7 | 9.1 | 12.2 |

The selectivity between two metals M/M' corresponds to the selectivity of the ligand for the metal M compared with that for the metal M', this selectivity being equal to:

$$\log(K_{app}(M)/K_{app}(M'))=\log K_{app}(M)-\log K_{app}(M')$$

EDTA and Trien are chelating agents for copper Cu(II). EDTA is a very strong hexadentate chelating agent having donor atoms nitrogen and oxygen, one of the main disadvantages of which is the lack of selectivity (it very strongly complexes all the essential and toxic ions cited in table I). Trien, for its part, is a very strong polyamine chelating agent which strongly complexes the metal ions mercury Hg(II) and copper Cu(II), and which exhibits relative selectivity toward the zinc ions Zn(II).

Pen is a chelating agent containing a thiol functional group as well as donor atoms nitrogen and oxygen. The presence of the thiol group makes it possible to achieve a relatively high affinity with the toxic ion Hg(II), while being selective toward the zinc ions Zn(II). However, the selectivity of Pen for the copper ions Cu(I) (compared with the zinc ions Zn(II)) remains low.

BAL is a dithiol chelating agent which has a very high affinity for the mercury ions Hg(II), and probably also for the copper ions Cu(I).

Thus, it appears that the introduction of thiol functional groups promotes the complexing of the soft ions, such as the mercury Hg(II) and copper Cu(I) ions, compared with the other ions.

There is still nevertheless a need today for more selective chelating agents, in particular toward copper, and more particularly intracellular Cu(I), and which are especially less toxic, the side effects of which are thought to be less violent than those of the molecules currently used.

SUMMARY

The inventors have found, surprisingly, that the novel compounds of the invention described below appear to be a better alternative, in particular in terms of selectivity, compared with the molecules previously developed, for the diagnosis, prevention and/or treatment of neurodegenerative diseases and/or of poisoning with metal ions, and more particularly with copper and mercury ions, these compounds being in particular useful for the treatment of Wilson's disease (the patients of which have an excess of copper in the liver) and for the treatment of Alzheimer's disease, or for detoxifying liver that has been poisoned with mercury Hg(II).

Accordingly, the present invention relates to novel cyclodecapeptides compounds of formula (I) for their use as drugs, in particular for the diagnosis, prevention and/or treatment of neurodegenerative diseases, such as Wilson's and Alzheimer's diseases, and for the diagnosis, prevention and/or treatment of poisoning with metal ions such as copper and mercury ions. The compounds of the invention may thus be used for the diagnosis and prevention of neurodegenerative diseases in people with an increased risk because of genetic or environmental factors.

Accordingly, the first subject of the present invention relates to cyclodecapeptide compounds corresponding to the following formula (I):

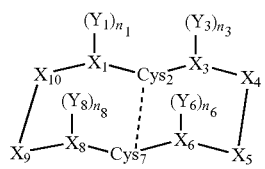

in which:
the cysteine amino acids $Cys_2$ and $Cys_7$ may or may not be linked by a covalent bond $Cys_2$-$Cys_7$ via their sulfur atoms, $X_1$, $X_3$, $X_4$, $X_5$, $X_6$, $X_8$, $X_9$, $X_{10}$, which are identical or different, are amino acids which may be present in the form of two optically active enantiomers: the dextrorotatory enantiomer (D) or the levorotatory enantiomer (L), $n_1$, $n_3$, $n_6$, $n_8$, which are identical or different, are equal to 0 or 1, $Y_1$, $Y_3$, $Y_6$, $Y_8$, which are identical or different, represent groups —C(O)CHNL, —C(O)EL or —NHEL, and preferably a group —C(O)CHNL, in which L is a biological ligand, and preferably a biological ligand for hepatic or neuronal cells, selected from monosaccharides such as glucose, galactose and N-acetylgalactosamine, and E is a spacer arm selected from polyols such as polyethylene glycol preferably having 1 to 8 oxyethylene OE units, and alkyl chains having 1 to 12 carbon atoms, optionally substituted with one or more substituents chosen from $C_1$-$C_6$ alkyl or alkoxy chains, the groups —OH, —COOH, —NO₂, —NH₂, —C(O)NH₂, —SH or halogen atoms, optionally, at least one of the amino acids $X_4$, $X_5$, $X_9$, $X_{10}$, and/or at least one of the groups $Y_1$, $Y_3$, $Y_6$, $Y_8$, may be substituted with a group selected from: —CO-marker, —NH-marker, —C(S)NH-marker, —SO₂-marker, =CH-marker, -E'-marker, where E' is a spacer arm selected from phenyl, triazole, oxadiazole, oxazole, imidazole, thiadiazole, pyrrole, tetrazole, furan, thiophene, pyrazole, pyrazoline, pyrazidine, thiazole, isothiazole, pyridine, pyrimidine, piperidine, pyran, pyrazine, pyridazine and derivatives thereof, and it being understood that the bonds $X_4$-$X_5$ and $X_9$-$X_{10}$, which are identical or different, are chosen from the bonds (D)Pro-(L)X or (L)Pro-(D)X', in which X and X' are amino acids, preferably chosen from glycine, lysine, glutamate or aspartate, for their use as drugs.

According to an advantageous embodiment, at least one of the amino acids $X_1$, $X_3$, $X_6$, $X_8$ is a lysine. Alternatively, at least one of the amino acids $X_1$, $X_3$, $X_6$, $X_8$ is a lysine bearing a group $Y_1$, $Y_3$, $Y_6$, $Y_8$.

According to another advantageous embodiment, the compound of formula (I) according to the invention is a compound in which at least one of the amino acids $X_4$, $X_5$, $X_9$, $X_{10}$, and/or at least one of the groups $Y_1$, $Y_3$, $Y_6$, $Y_8$, is substituted with a group selected from: —CO-marker, —NH-marker, —C(S)NH-marker, —SO₂-marker, =CH-marker, -E'-marker.

The expression "marker" is understood to mean any entity capable of being detected by appropriate means, the markers used in the context of the invention typically corresponding to the markers used by persons skilled in the art in the field of biology for labeling molecules of biological interest, in particular in the context of carrying out a diagnosis, galenic studies, or alternatively the monitoring of the metabolization of active compounds. The labeling may be of a direct nature, and in this case, the marker is termed "direct marker" and exhibits at least one detectable physical property, or the marker may be of an indirect nature, and in this case, the marker is termed "indirect marker" and is capable of reacting selectively with a third entity, it being possible for the latter either to exhibit at least one detectable physical property, such as for example an antibody exhibiting a fluorescent activity, or to be involved in a reaction process at the end of which a physical property may be detected, such as for example when the product of degradation of the entity may exhibit at least one detectable physical property such as fluorescence. Indirect labeling is often carried out using antibodies or nanoparticles having a fluorescent activity. In this case, the indirect marker for the compounds of formula (I) has an affinity for the third entity.

Accordingly, the marker of the invention may be either a chemical entity of an organic nature, or a chemical entity of an inorganic nature, such as a complex or a crystal, it being possible for the latter to be optionally coated with an organic layer, this chemical entity of an inorganic nature being generally of a sufficiently small size, typically on the nanometer scale, so as not to disrupt the biological system into which it is introduced.

The directly or indirectly detectable physical property may be a specific reactivity toward an electromagnetic source such as a magnetic field, for example by magnetic resonance imaging, or toward light radiation which may be focused, for example by fluorescence imaging with fluorophores, or else toward nuclear radiation, for example using isotopes.

The most preferred markers are the direct markers, and more particularly the fluorophores. Typically, they are organic fluorophores or nanoparticles. The fluorophores used in the context of the invention may be aromatic fluorescent compounds whose π-π transitions are characterized by molar absorption coefficients and fluorescence quantum yields that are high, it being possible for said fluorophores to be chosen from rhodamine, fluorescein, pyronin, coumarin, benzophenone, anthrone, fluorenone, pyridine, quinoleine, acridine, naphthalene, anthracene, naphthacene, pentacene, xanthene and derivatives thereof.

The various families of markers and the various associated detection techniques are known to a person skilled in the art and are described in the manual Anti-Cancer Ag. in Med. Chem., 2008, 8, 497-522. More specifically, reference may be made to the fluorophores cited in Cytometry Part A, 2006, 69A: 863-871, and to the nanoparticles mentioned in the document Anal. Bioanal. Chem., 2006, 384: 620-630.

Accordingly, the labeled compounds of formula (I) of the invention may be used to visualize the movement of said compounds in the body, by luminescence.

According to another advantageous embodiment of the invention, the compounds of the invention are compounds wherein $n_1$, $n_3$, $n_6$, $n_8$=0, said compounds then corresponding to the following formula (Ia):

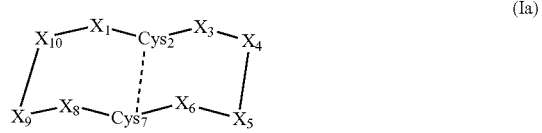

(Ia)

Another subject of the invention relates to the compounds of formula (I) according to the invention, for the preparation of a drug intended for the diagnosis, prevention and/or treatment of neurodegenerative diseases, and more particularly for the treatment of Wilson's and Alzheimer's diseases.

The compounds of the invention may also be used as chelating agents for metal ions for the preparation of a drug intended for the diagnosis, prevention and/or treatment of poisoning with metal ions such as silver, cadmium, cobalt, copper, mercury, nickel, gold, lead and zinc ions, and more particularly for the treatment of poisoning with mercury or copper ions, such as the intracellular copper ions Cu(I), poisoning with such ions generally leading to severe inflammation, renal deficiency, hemorrhage, severe neurological disorders of the central nervous system; the expression hydrargyria (or hydragyrism) is used in particular in the case of mercury poisoning.

It should be noted that another possible use of the compounds of formula (I) according to the invention, in which the cysteine amino acids $Cys_2$ and $Cys_7$ are not linked by a covalent bond, relates to their use in vitro as depolluting agents for depolluting contaminated water, preferably in a reducing medium. The value of the maximum pH of the medium depends on the metal ion to be complexed. Thus, for the Hg(II) and Cu(I) ions, the pH of the reducing medium is preferably greater than or equal to 1, and for the Zn(II), Pb(II) and Cd(II) ions, the pH of the reducing medium is preferably greater than or equal to 4 or 6.

The compounds of formula (I) of the invention, in which the cysteine amino acids $Cys_2$ and $Cys_7$ are linked by a covalent bond $Cys_2$-$Cys_7$ via their sulfur atoms, are converted in a reducing medium to compounds of formula (I), in which the cysteine amino acids $Cys_2$ and $Cys_7$ are free (absence of a covalent bond between the sulfur atoms of the cysteines $Cys_2$ and $Cys_7$). This reducing reaction allows the release of the thiol functional groups of the cysteines $Cys_2$ and $Cys_7$ (which were masked by the $Cys_2$-$Cys_7$ covalent bond), once the compounds of formula (I) which are vectorized in the body have entered the target cells. The compounds of formula (I), in which the cysteine amino acids $Cys_2$ and $Cys_7$ are linked by a covalent bond $Cys_2$-$Cys_7$ via their sulfur atoms, may therefore be used as precursors for vectorization in the body of compounds of formula (I), in which the cysteine amino acids $Cys_2$ and $Cys_7$ are not linked by a covalent bond via their sulfur atoms.

The reducing agent allowing the production of the compounds of formula (I), in which the cysteine amino acids $Cys_2$ and $Cys_7$ are free, may be a molecule bearing a thiol functional group, such as ethanedithiol (EDT), glutathione (GSH), cysteine and dithiotreitol (DTT), or a molecule bearing a phosphine functional group such as tris(2-carboxyethyl)phosphine (TCEP).

Accordingly, the release of the thiol functional groups of the cysteine amino acids $Cys_2$ and $Cys_7$ is carried out by reduction in vivo in the body, for example in the hepatic cells where glutathione (GSH), which is present at about 1 mM, may act as the reducing agent.

Finally, the last subject of the invention relates to pharmaceutical compositions comprising, as active ingredient, at least one compound of formula (I) according to the invention, and at least one pharmaceutically acceptable vehicle. Said pharmaceutical compositions comprise both compositions in solid form (tablets, gelatin capsules, capsules, and the like), and compositions in liquid form (solutions, suspensions or emulsions), and comprise excipients suitable for oral, topical or parenteral administration. The administration of the compounds or the compositions according to the invention is preferably carried out by the oral route or by the parenteral route (intravenously as a perfusion or injection, in particular). The doses of compounds are preferably less than 2 g of product per day, and vary according to the formulation selected, the mode of administration and the poisoning or the disease to be treated. Other factors such as the age, weight, size, sex, as well as certain biological parameters (rate of excretion, association with other drugs, allergies and the like) should also be taken into account.

BRIEF DESCRIPTION OF THE DRAWINGS

In addition to the preceding arrangements, the invention also comprises other arrangements which will emerge from the additional description which follows, which relates to examples demonstrating the complexation properties, and more particularly the copper Cu(I) complexation properties, in the hepatic cells, of the compounds of the invention, and to the accompanying figures in which.

DETAILED DESCRIPTION

Examples

A—Methods of Characterization

1/High Performance Liquid Chromatography (HPLC)

Figure 1:
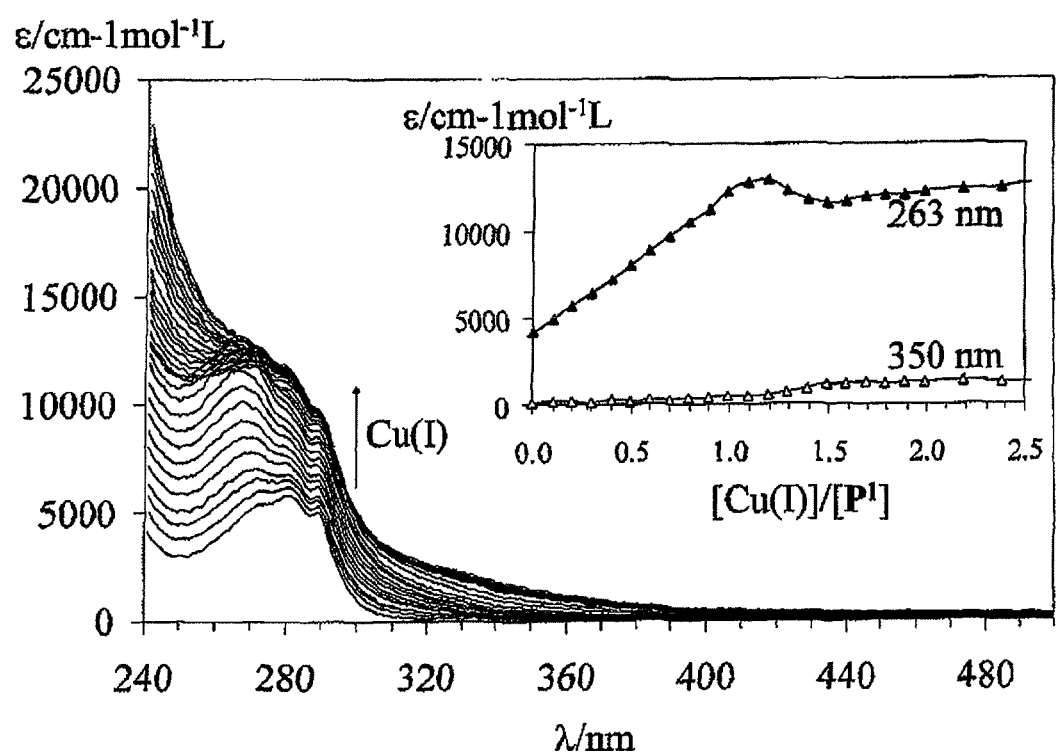
FIG. 1 represents the UV assay of a compound P' according to the invention with $Cu(CH_3CN)PF_6$, in a phosphate buffer solution at 20 mM, of pH=7.4, at a temperature of 298 K.

HPLC chromatography is carried out on a VWR system equipped with RP18 columns (L=250 mm, Ø=4.6 mm and p=5 μm, for the analytical column; L=250 mm, Ø=50 mm and p=10 μm, for the preparative column).

The flow rates used are 1 mL/min for the analytical column and 75 mL/min for the preparative column, with UV detection at 214 nm.

The elution conditions are the following:

solvent A: water/trifluoroacetic acid (TFA) mixture (99.925/0.075), and solvent B: acetonitrile (CH$_3$CN)/water/trifluoroacetic acid (TFA) mixture (90/10/0.1).

2/UV-Visible Spectroscopy

The UV-visible spectra were recorded on a Varian Cary 50 spectrophotometer.

3/Mass Spectrometry

The mass spectra were recorded on an LXQ THERMO SCIENTIFIC type spectrometer, equipped with a source of ionization in electrospray mode (ESI).

4/Fluorescence Microscopy

The fluorescence microscopy images are obtained on an AxioVert 200M (Carl Zeiss) inverted microscope equipped with an NHBO 103 mercury vapor lamp and a HAL 100 W halogen lamp, and with a fluorescence measuring device.

The images are produced with a ×63 magnification.

B—Synthesis

Synthesis of Cyclodecapeptide Compounds P$^1$ and P$^2$ Corresponding to the Formula (Ia) of the Invention (the Amino Acids Cys$_2$ and Cys$_7$ not being Linked to Each Other by a Covalent Bond):

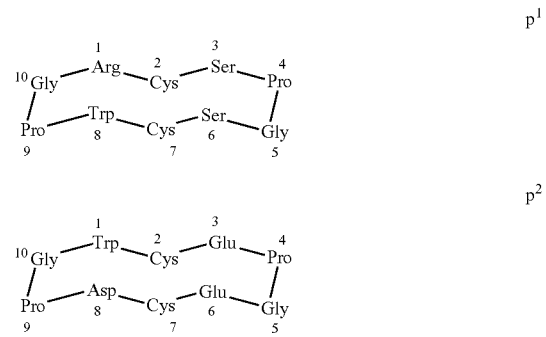

The protected linear precursors HArg(Pbf)-Cys(Trt)-Ser (tBu)-Pro-Gly-Ser(tBu)Cys(Trt)-Trp(Boc)Pro-Gly-OH and H-Trp(Boc)-Cys(Trt)-Glu(tBu)-Pro-Gly-Glu(tBu)-Cys(Trt)-Asp(tBu)-Pro-GlyOH were prepared by solid phase peptide synthesis on a 2-chlorotrityl chloride resin (substitution 0.5 mmol/g, 500 mg) by Fmoc chemistry (peptide synthesis on a solid support using 9-fluorenylmethoxycarbonyl as protecting group, R. Sheppard, J. Peptide Sci., 2003, 9: 545-552). The couplings are carried out by mixing the N-α-Fmoc-protected amino acids (2 equivalents), with benzotriazol-1-yl-oxytripyrrolidinophosphonium (PyBOP) (2 equivalents) and N,N-diisopropylethylamine (DIEA) (6 equivalents), for 30 minutes. After each coupling, the resin is treated with a DMF/pyridine/Ac$_2$O mixture (v/v/v=7/2/1) in order to acetylate the unreacted amino groups (2×5 minutes). The deprotection of the Fmoc groups is carried out by treatment with a DMF/piperidine mixture (v/v=4/1, 3×5 minutes). The yield obtained for each peptide is monitored by UV-visible spectrometry ($\varepsilon^{300\ nm}$=7800 L·mol$^{-1}$·cm$^{-1}$ for the piperidine-dibenzofulvene adduct). The peptide is then detached from the resin by treatment with 15 mL of a mixture of dichloromethane (CH$_2$Cl$_2$) and trifluoroacetic acid (TFA) (v/v=99/1) (2×3 minutes). The cleavage is carried out rapidly, and the solution is introduced into 15 mL of a methanol/pyridine solution (v/v=8/2). After concentration, the residue is precipitated several times in ice-cold diethyl ether in order to obtain a white powder. The linear precursor is then reacted in CH$_2$Cl$_2$ (0.5 mM) with PyBOP (3 equivalents) and DIEA (4 equivalents). The formation of the cyclic peptide is monitored by HPLC analysis, and the reaction is stopped after 10 minutes. The dichloromethane (CH$_2$Cl$_2$) is then evaporated. The oily residue is precipitated with a CH$_2$Cl$_2$/Et$_2$O mixture in order to obtain a cyclic peptide in the form of a powder. The chains are then deprotected by treatment with a solution of 1.4 g of dithiothreitol (DTT) in a TFA/TIS (triisopropylsilane)/$H_2O$ mixture (v/v/v=95/2.5/2.5) (peptide concentration=10 mM). After stirring for 2 hours, the solution is evaporated under reduced pressure in order to give a yellow oil which is precipitated several times with ice-cold diethyl ether. The solid residue obtained is then dissolved in a water/acetonitrile mixture, and then passed over a polytetrafluoroethylene (PTFE) filter whose pore diameter is 0.45 μm, and then purified by reversed phase HPLC chromatography (gradient from 5 to 45% of B over 30 minutes), in order to give a compound P' in the form of a white powder (52 mg, 19% yield), or a compound $P^2$ in the form of a white powder (144 mg, 53% yield).

Compound $P^1$:

HPLC analysis, purity: 96%, $t_R$=15.7 min (gradient 5 to 60% of B over 30 minutes).

MS: calculated for $C_{43}H_{62}N_{14}O_{12}S_2$, $[M+H^+]^+$=1031.41, exp=$[M+H^+]^+$=1031.45.

Compound $P^2$:

HPLC analysis, purity: 98%, $t_R$=23.6 min (gradient 5 to 45% of B over 30 minutes).

MS: calculated for $C_{45}H_{59}N_{11}O_{16}S_2$, $[M+H^+]^+$=1074.36, exp=$[M+H^+]^+$=1074.65.

Synthesis of Cyclodecapeptide Compounds $P^3$ and $P^3$-TRITC Corresponding to the Formula (I) of the Invention (the Amino Acids $Cys_2$ and $Cys_7$ being Linked by a Covalent Bond):

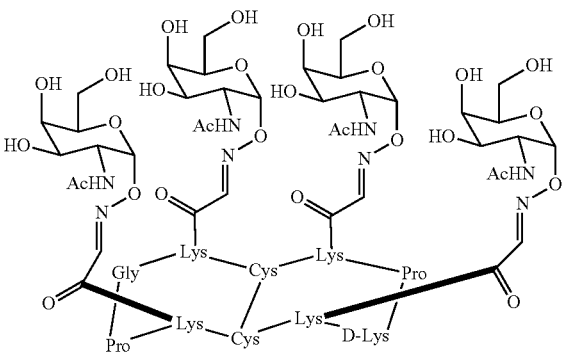

The cyclodecapeptide compounds $P^3$ and $P^3$-TRITC corresponding to the formula (I) of the invention are synthesized according to scheme 1 below. The oxyamine blocks Fmoc-Lys[BocSer(tBu)]-OH and O-α-D-galactopyranosyl (αGalNAcONH$_2$, compound 6) are synthesized as described in the literature (Renaudet et al., Org. Biomol. Chem., 2006, 4: 2628-2636; S. Fouillard et al., J. ORG. Chem., 2008, 73: 983-991).

Scheme 1

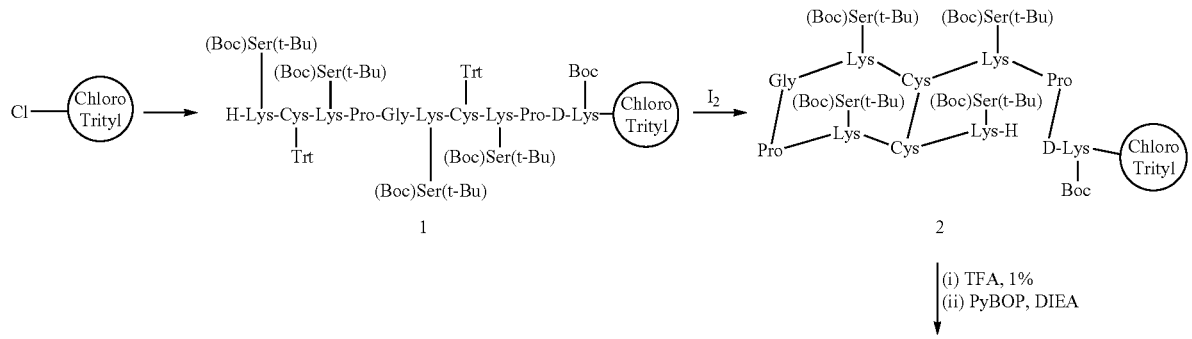

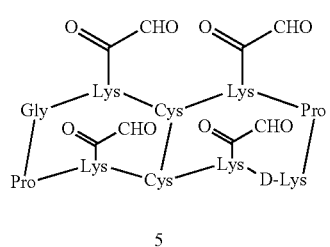
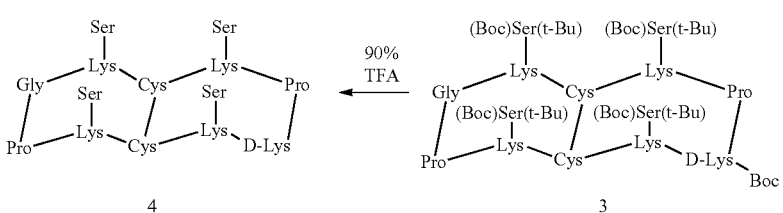
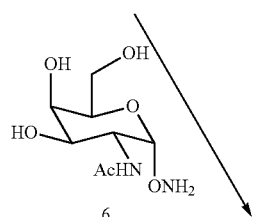
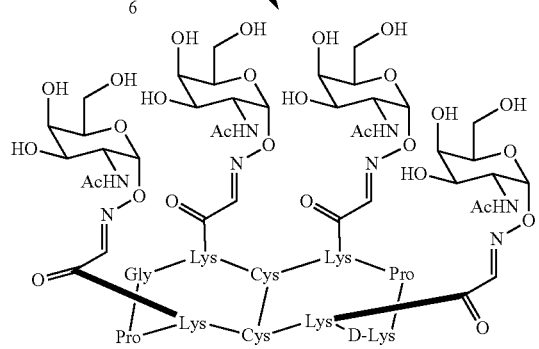
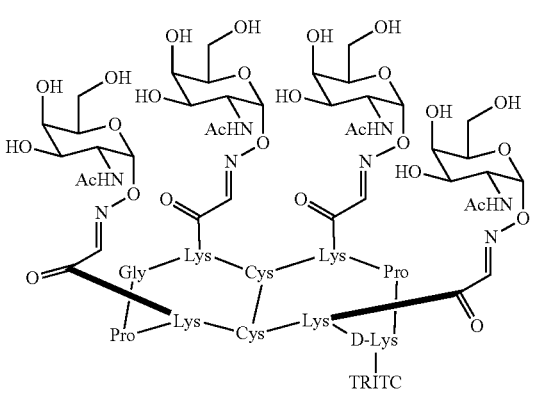

Synthesis of Compound 4:

The linear precursor 1 bearing protecting groups is prepared by solid phase peptide synthesis on a 2-chlorotrityl chloride resin (substitution 0.4 mmol/g, 0.507 g, 0.202 mmol) by Fmoc chemistry. The resin is swollen with dichloromethane ($CH_2Cl_2$) (10 mL, 1×10 min) and DMF (10 mL, 1×10 min). The couplings are carried out by mixing the N-α-Fmoc-protected amino acids or Fmoc-Lys[BocSer(tBu)]-OH (2.5 equivalents, 0.5 mmol), with benzotriazol-1-yl-oxytripyrrolidinophosphonium (PyBOP) (2.5 equivalents, 0.5 mmol) and N,N-diisopropylethylamine (DIEA) (pH≈8-9) in DMF (10 mL), for 30 minutes. After washing with DMF (10 mL, 4×1 min) and $CH_2Cl_2$ (10 mL, 2×1 min), the deprotection of the N-α-Fmoc groups is carried out by treatment with a DMF/piperidine mixture (v/v=4/1, 10 mL, 3×10 min). After the last wash with DMF (10 mL, 6×1 min), the end of the deprotection reaction is checked by UV-visible spectrometry ($\epsilon^{300\ nm}$=7800 L·mol-1·cm-1 for the piperidine-dibenzofulvene adduct). After the last coupling reaction, the functionalized resin 1 is obtained (0.13 mmol, 64% yield).

The functionalized resin 1 (0.13 mmol) is then swollen with dichloromethane ($CH_2Cl_2$) (10 mL, 1×10 min) and DMF (10 mL, 1×10 min). Iodine (0.660 g, 2.60 mmol) and DMF (10 mL) are added. The reaction mixture is stirred at room temperature for 1.5 hours. After filtration, the resin is washed with DMF (10 mL, 6×5 min), a DMF/water mixture (v/v=1/1) (10 mL, 2×5 min), DMF (10 mL, 1×5 min) and $CH_2Cl_2$ (10 mL, 3×5 min).

The peptide is then detached from the resin by treatment with a $CH_2Cl_2$/TFA mixture (v/v=99/1, 10 mL, 10×2 min). The filtrate is then recovered, and N,N-diisopropylethylamine (DIEA) (1 mL) is added in order to avoid deprotection during the evaporation step. After concentration, the residue is precipitated in diethyl ether. The linear precursor is then reacted in DMF (~0.5 mM) with PyBOP (0.074 g, 0.14 mmol) and DIEA (0.08 mL, 0.39 mmol), for 2 hours. The DMF is evaporated under reduced pressure. The oily residue is precipitated with a $CH_2Cl_2/Et_2O$ mixture, in order to give a cyclic peptide 3 in the form of a powder. The chains are then deprotected by treatment with a TFA/$H_2O$ mixture (v/v=90/10, 20 mL). After stirring for 2 hours, the solution is evaporated in order to give a yellow oil which is precipitated with diethyl ether, in order to give a deprotected peptide 4 in the form of a white powder (0.097 g, 0.067 mmol, 33% yield).

HPLC analysis, purity: 83%, $t_R$=6.13 min (linear gradient A/B:95/5 to 60/40, over 15 minutes).

MS: calculated for $C_{60}H_{105}N_{19}O_{18}S_2$, $[M+H^+]^+$=1444.74, exp: $[M+H^+]^+$=1444.58, $[M+2H^+]^+$=722.92, $[M+3H^+]^{3+}$=482.33.

Synthesis of Compound 5:

Sodium periodate (0.380 g, 1.77 mmol) is added to a solution of compound 4 (0.064 g, 0.044 mmol) in water (8 mL). After 15 minutes, the reaction mixture is injected into an RP-HPLC column ($t_R$=14 min, linear gradient A/B:95/5 to 60/40, over 15 minutes), in order to give a compound 5 in the form of a white powder (0.009 g, 0.0068 mmol, 15% yield) after freeze-drying.

MS: calculated for $C_{56}H_{85}N_{15}O_{18}S_2$, $[M+H^+]^+$=1320.57, exp=$[M+H^+]^+$=1320.5.

Synthesis of Compound $P^3$:

O-α-D-galactopyranosyl oxyamine (compound 6) is added (0.045 g, 0.192 mmol) to a solution of compound 5 (0.025 g, 0.019 mmol), in an AcOH/$H_2O$ mixture (4 mL, v/v=1/9).

The reaction mixture is stirred at room temperature for 1 hour. The mixture is then injected into an RP-HPLC column ($t_R$=14-16 min, linear gradient A/B:95/5 to 60/40, over 15 minutes), in order to give a compound $P^3$ in the form of a white powder (0.021 g, 0.0096 mmol, 50% yield) after freeze-drying.

HPLC analysis, purity: 95%, $t_R$=7.0 min (linear gradient A/B:95/5 to 60/40, over 15 minutes).

MS: calculated for $C_{88}H_{141}N_{23}O_{38}S_2$, $[M+H^+]^+$=2192.92, exp=$[M+H^+]^+$=2193.5.

Synthesis of Compound $P^3$-TRITC:

A marker, TetraMethylRhodamineIsoThioCyanate (TRITC) is added (0.003 g, 0.0067 mmol) with a few drops of DIEA (pH≈8-9) to a solution of a compound $P^3$ (0.012 g, 0.0055 mmol) in DMF (2 mL). The reaction mixture is then stirred at room temperature for 2 hours, and then injected into an RP-HPLC column ($t_R$=19 min, linear gradient A/B: 95/5 to 60/40, over 15 minutes) in order to give a compound $P^3$-TRITC in the form of a white powder (0.0012 g, 0.00046 mmol, 8% yield) after freeze-drying.

MS: calculated for $C_{113}H_{163}N_{26}O_{41}S_3^+$, $[M]^+$=2637.1, exp=$[M]^+$=2636.6, $[M^++H^+]^{2+}$=1318.9.

C—Characterization of the Copper Cu(I) Complexes Formed with the Peptides $P^1$ and $P^2$ Procedure Since the thiol functional groups —SH of the cysteine amino acids are subject to oxidation in the air, all their solutions were prepared in a glove box under an argon atmosphere. Solutions of ligands were then prepared, before each experiment, by using water deoxygenated and purified by a Millipore Milli-Q® system containing 20 mM of a phosphate buffer solution (pH=7.4) and acetonitrile (v/v:9/1).

The final concentration of the solution was determined by measuring the concentration of the free thiol functional groups, following the Ellman procedure described in the literature (P. W. Riddles et al., Methods Enzymol., 1983, 91, pp. 49-60). This method uses 5,5'-dithiobis-2-nitrobenzoic acid (DNTB) as indicator, each free thiol group present in the ligand leading to 1 equivalent of $TNB^{2-}$ ($\epsilon^{412\ nm}$ ($TNB^{2-}$)=14 150 $M^{-1}.cm^{-1}$, $\epsilon^{412\ nm}$ being the molar extinction coefficient of $TNB^{2-}$ at 412 nm). The concentrations of the solutions of ligands are between 30 and 100 μM.

The copper Cu(I) solutions were prepared by dissolving an appropriate quantity of $Cu(CH_3CN)_4\ PF_6$ in deoxygenated acetonitrile. The final concentration is determined by adding an excess of sodium bathocuproine disulfonate ($Na_2BCS$) and by measuring the absorbance of $Cu(BCS)_2^{3-}$ ($\lambda_{max}$=483 nm, $\epsilon$=13 300 $M^{-1}.cm^{-1}$).

For the measurements of affinity constants, the complex is prepared by adding to the ligand solution a solution of acetonitrile ($CH_3CN$) containing 0.8-0.9 equivalent of copper Cu(I), in a phosphate buffer solution at 20 mM (pH=7.4) and acetonitrile ($CH_3CN$) (v/v:9/1).

The formation of the complex is then carried out by stirring the mixture for 10 minutes, under argon. Aliquots of a bathocuproine disulfonate (BCS) solution in the same buffer solution are then added to the ligand-copper complex. The UV-visible spectra are recorded, and the stability of the absorbance is checked before the addition of the other aliquots.

1—UV-Visible Spectroscopy

The formation of the Cu(I) complexes was monitored by UV-visible spectroscopy.

FIG. 1 gives an example of a UV assay of the compound $P^1$ with $Cu(CH_3CN)PF_6$ (Cu(I)) in phosphate buffer at 20 mM, at a pH of 7.4 and at 298 K.

The thiolate→Cu(I) charge transfer band appears clearly around 260 nm. This band increases up to 1 equivalent for the two peptides $P^1$ and $P^2$. The Cu(I) complexes obtained therefore have an overall stoichiometry of 1:1 (Cu:L) for these ligands (L) comprising two cysteines.

2—Mass Spectrometry

Figure 2:
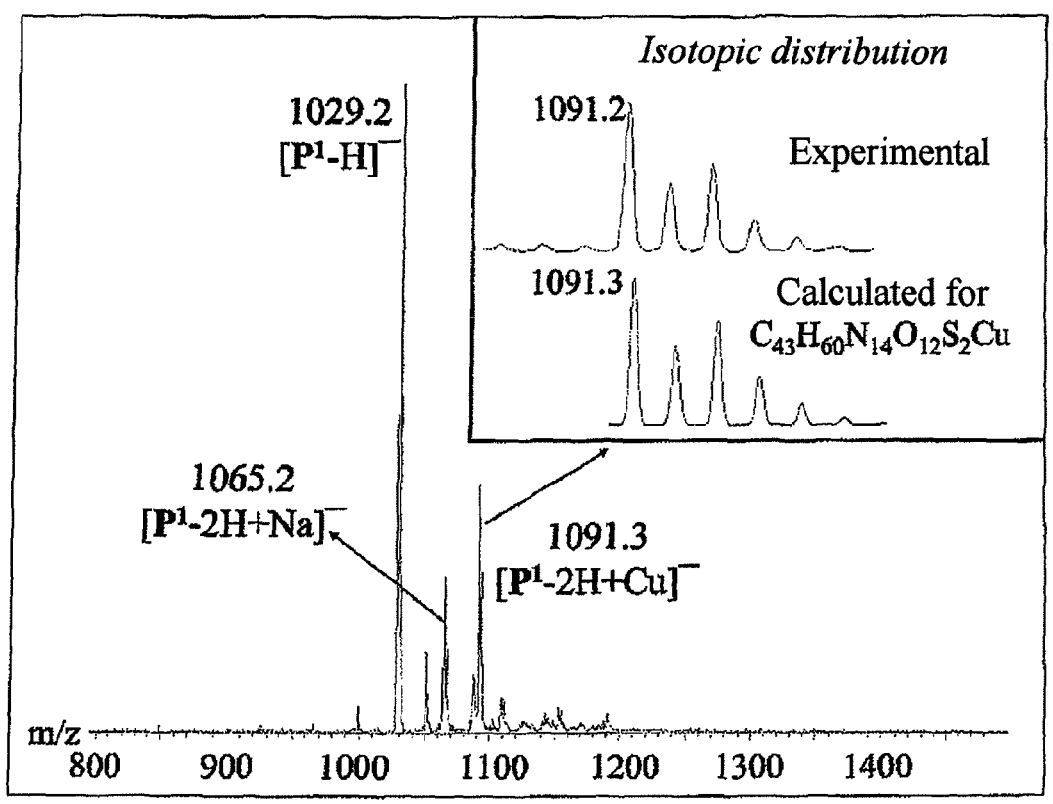
FIG. 2 represents the ES-MS mass spectrum of a compound P' according to the invention, in the presence of one equivalent of Cu(I)

The stoichiometry for the complex is also demonstrated by mass spectrometry in electrospray ionization mode, the mass spectra having been recorded with an LXQ THERMO SCIENTIFIC type spectrometer. The Cu($P^1$) complex is clearly detected on the spectra for the compound P' in the presence of 1 equivalent of Cu(I) (cf. FIG. 2).

3—Affinity Constants

For the measurements of affinity constants, the complex is prepared by adding to the ligand solution a solution of acetonitrile ($CH_3CN$) containing 0.8-0.9 equivalent of copper Cu(I), in a phosphate buffer solution at 20 mM (pH=7.4) and acetonitrile ($CH_3CN$) (v/v:9/1).

The affinity of the compounds of the invention for Cu(I) is an important matter since it makes it possible to quantify the capacity of the compounds of the invention to complex this ion. The affinity constants were measured using a known competitor having a high affinity for Cu(I), bathocuproine disulfonate (BCS), which forms complexes with copper Cu(I) of known stability according to the reaction below (Z. Xiao et al., J. Am. Chem. Soc., 2004, 126: 3081-3090; P. Rousselot-Paillet et al., Inorg. Chem., 2006, 45: 5510-5520):

$$Cu(I) + 2BCS = Cu(BSC)_2$$

$$K = \frac{[Cu(BCS)_2]}{[Cu][BCS]^2} = 10^{19.8} \text{ at 298 K}$$

These competition experiments made it possible to quantify the affinity of the compounds $P^1$ and $P^2$ of the invention for copper Cu(I): the apparent copper Cu(I) complexation constants in a phosphate buffer solution at 20 mM of pH 7.4, at a temperature of 298 K, as defined below, are given in table II.

$$K_{app} = \frac{[Cu]_{complexed}}{[Cu]_{free}[L]_{free}}$$

TABLE II

|  | $P^C$ | Compound $P^1$ | Compound $P^2$ |
|---|---|---|---|
| $\log K_{app}$ | 16.5 | 16.7 | 15.5 |

It appears clearly that the peptides of the invention in which the thiol functional groups of the cysteine amino acids are free have high affinities for Cu(I). Moreover, the affinities of $P^1$ and $P^2$ are comparable to those obtained with the cyclopeptide $P^c$ (reference) modeling the Atx1 yeast copper chaperone loop (P. Rousselot-Paillet et al., Inorg. Chem., 2006, 45: 5510-5520). These results demonstrate the capacity of the compounds of the invention to complex copper Cu(I) in excess in an intracellular medium.

D/ Characterization of the Complexes Between the Peptides and $P^2$ and Other Metal Ions Procedure:

The procedures are those described in the article Rousselot-Paillet et al., Inorg. Chem., 2006, 4: 2628-2636.

The complexation of mercury Hg(II) by the compounds $P^1$ and $P^2$ is very effective (high affinity constants), and may therefore be of interest for the detoxification of this toxic metal. The complexation of zinc Zn(II) was also studied because this nontoxic metal ion is present in vivo, in the hepatic cells targeted. The compounds have a much lower affinity for zinc Zn(II) than for copper Cu(I) and mercury Hg(II). This selectivity is crucial because it makes it possible to detoxify the target metal (copper Cu(I) or mercury Hg(II)) without complexing zinc. This parameter is expressed by the selectivity Sel. M/M' between two metals M and M'. Table III below assembles the apparent constants obtained at pH=7.4, with the cyclodecapeptide compounds of the invention, and their selectivity for the ions targeted relative to zinc Zn(II).

TABLE III

| $\log K^{app}$ | $P^C$ | Compound $P^1$ | Compound $P^2$ |
|---|---|---|---|
| Cu(I) | 16.5 | 16.7 | 15.5 |
| Zn(II) | 6.8 | 6.6 | 5.9 |
| Hg(II) | >18.6 | >18.7 | >17.5 |
| Sel. Cu/Zn | 9.7 | 10.1 | 9.6 |
| Sel. Hg/Zn | >11.8 | >12.1 | 11.6 |

The compounds $P^1$ and $P^2$ of the invention exhibit good affinities and good selectivities relative to zinc Zn(II) present in the cells, which makes them very promising for the selective complexation of copper having an oxidation state +I, which oxidation state is favored in the intracellular medium and which may therefore be targeted in Wilson type diseases. These compounds are also candidates for the selective complexation of mercury Hg(II) during poisoning by this metal.

E/ Characterization of the Copper Cu(I) Complexes Formed with the Peptide $P^3$

Figure 3:
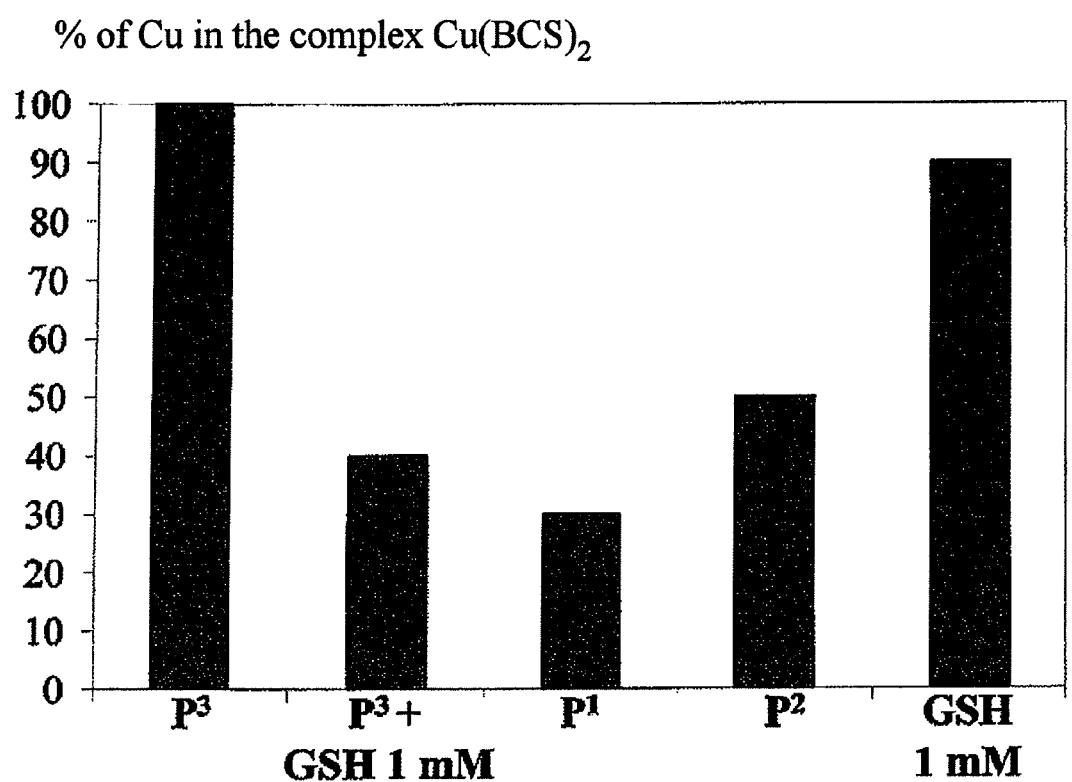
FIG. 3 shows the variation of the quantity of free copper Cu(I), detected with bathocuproine disulfonate (BCS), and measured by UV absorption of the complex Cu(BCS)$_2$, in a phosphate buffer solution at 20 mM, of pH=7.4, and with [P$^3$]=[P$^1$]=[P$^2$]=50 μM, [Cu(I)]=40 μM and [BCS]=100 μM.

BCS was used to determine the concentration of copper Cu(I) not complexed by the compound $P^3$. The results are represented in FIG. 3. When the compound $P^3$ is alone, it does not complex copper (100% of Cu(I) is complexed by BCS), since the thiol functional groups of the compound $P^3$ are masked by the disulfide bridges (S—S) of the molecule. On the other hand, in the presence of a reducing agent (GSH 1 mM as in the cells), capable of reducing the S—S bridges in order to regenerate the free thiol functional groups, the compound $P^3$ evolves into an effective complexing agent for copper (the two cysteines $Cys_2$ and $Cys_7$ then being free as in the compounds P' or $P^2$), since the quantity of copper detected by BCS drops to 40%. This percentage corresponds to an intermediate apparent stability constant between the peptides $P^1$ and $P^2$: log $K^{app}$ ($P^3$ reduced)=16.

These results show that the compound $P^3$ complexes copper Cu(I) in a reducing medium, with an affinity similar to the compounds $P^1$ and $P^2$, the compounds of the invention, in which the cysteine amino acids $Cys_2$ and $Cys_7$ are linked by a $Cys_2$-$Cys_7$ covalent bond, becoming metal-chelating agents only in the target cells, and therefore causing no side effects linked to the undesirable complexation of metals at other sites in the body.

F/ Biological Results on Hepatic Cells

1—Entry of the Compound $P^3$-TRITC into Hepatic Cells

Procedure:

The cells ($10^5$-$10^6$/mL) are deposited on cover glass at the bottom of culture wells and immersed in the appropriate culture medium. After a variable incubation time in the presence of the compound $P^3$-TRITC, each cover glass is washed, fixed with a 10% formaldehyde solution (Sigma) and mounted on an observation slide in the presence of mounting fluid (Sigma). Each slide is then observed under a fluorescence microscope in order to locate the TRITC marker in the cells. About thirty fields are observed on each cover glass in order to obtain a significant statistical result. The experiment is repeated on cells from various batches.

Figure 4:
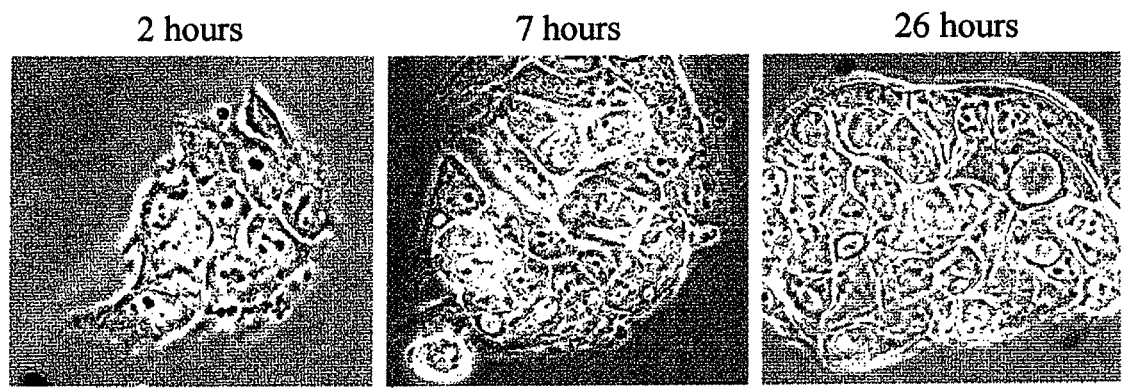
FIG. 4 represents images obtained by fluorescence microscopy (magnification ×63) showing the variation of a compound P$^3$-TRITC according to the invention (0.2 μm) in HepG2 cells, after 2 hours, 7 hours and 26 hours of incubation.

Results:

The entry of the compound $P^3$-TRITC (0.2 μM) into HepG2 type hepatic cells, WIF-B9 (C. Decaens et al., 1996, J. Cell Sci., 109 (Pt 6): 1623-1635) and Can10 (X. Peng et al., 2006, Cell Tissue Res., 323: 233-243) was studied by fluorescence microscopy by monitoring the emission in the red of the TRITC marker (cf. FIG. 4). Kinetics were established at two concentrations (0.2 and 2 μM) in order to evaluate the entry time of the molecule into these different cells.

The hepatocytes of the HepG2 line incorporate the compound $P^3$-TRITC from 2 hours of incubation. Over time, the cells become enriched with compound $P^3$-TRITC.

Figure 5:
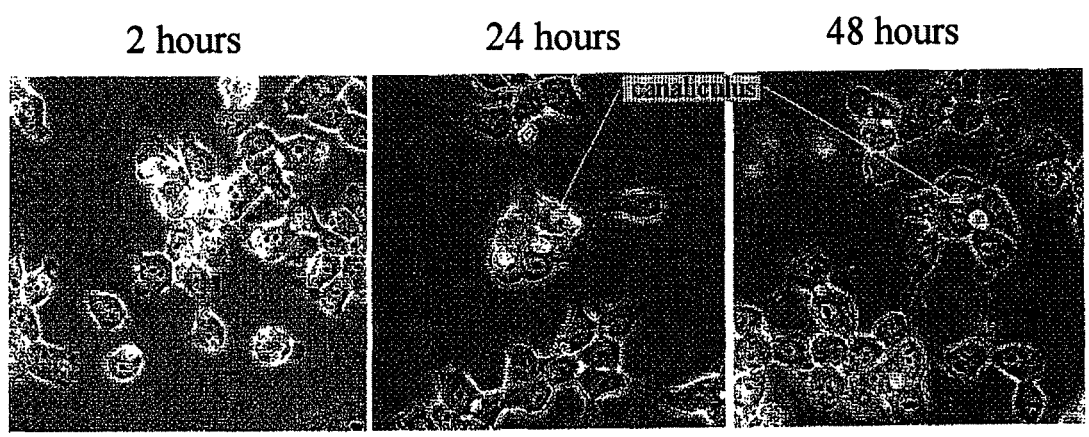
FIG. 5 represents images obtained by fluorescence microscopy (magnification ×63) showing the variation of a compound P$^3$-TRITC according to the invention (0.2 μm) in Can 10 cells, after 2 hours, 7 hours and 26 hours of incubation.

The study was continued with hepatocytes of the Can10 (cf. FIG. 5) and WIF-B9 lines, which have the characteristic feature of forming bile canaliculi after about ten days of culture. This characteristic makes it possible to monitor the presence of the compound $P^3$-TRITC in a polarized cell, which is closer to the physiology than the HepG2 line which does not become polarized. Compared with the situation of a hepatocyte in the liver, the culture medium represents the blood plasma and the bile canaliculus represents the natural site of excretion of copper.

The Can10 cells incorporate the compound P³-TRITC from 2 hours of incubation. After 24 hours of incubation, some canaliculi are fluorescent, which demonstrates that the compound P³-TRITC has crossed the cells. After 48 hours, all the canaliculi are fluorescent. The results obtained with the cells of the WIF-B9 line are similar.

These results demonstrate that the compound P³-TRITC is capable of entering into various types of hepatic cells within only a few hours.

2—Complexation of Copper Cu(I) in Hepatic Cells

Procedure:

The cells ($10^5$-$10^6$/mL) are deposited on cover glass at the bottom of culture wells and immersed in the appropriate culture medium. After an incubation of 1 to 5 hours in the presence of 1 µM of copper Cu(I), and optionally in the presence of 10 µM of compound P³, each cover glass is washed, and then fixed and the cells permeabilized with a pure methanol solution at −20° C. for 4 minutes. After washing, the cover glass are exposed to a medium containing the primary anti-ATP7B antibody (Hernandez et al., Gastoenterology, 2008, 134, 1215-1223) and, in the case of a double labeling, to a medium containing an anti-ZO-1 antibody (ZO-1 being a protein consisting of tight junctions joining the hepatocytes and delimiting the apical membrane, ZO-1 being a marker for the canaliculi). The cover glass are then exposed to a medium containing a secondary antibody, Alexa Fluor 546 goat anti-rat IgG (H+ L) (Invitrogen), fluorescent in the green for the protein ATP7B and in the red for the ZO-1 antibody, and then mounted on an observation slide in the presence of mounting fluid (Sigma), this secondary antibody making it possible to visualize the ZO-1 protein and to signal its position in the cells. Each slide is then observed under a fluorescence microscope in order to locate the ATP7B protein, and optionally ZO-1, in the cells. About thirty fields are observed on each cover glass in order to obtain a significant statistical result. The experiment is repeated on cells obtained from various batches.

Results:

It was shown that the position of the membrane ATP7B protein (Wilson protein) depended on the concentration of intracellular copper Cu(I) in the hepatocytes, such as for example WIF-B9. This protein can therefore be used as indicator for the increase in the intracellular concentration of copper Cu(I). For that, the position of the ATP7B protein in the cell is identified by labeling with a primary anti-Wilson antibody, itself detected by a secondary antibody that is fluorescent in the green. Under basal conditions, the ATP7B protein is located in the region of the Golgi apparatus, whereas in an excess of copper Cu(I), it moves toward the apical membrane, that is to say toward the membrane which surrounds the canaliculi, in order to excrete the excess copper Cu(I) (Y. Guo et al., Am. J. Physiol. Gastrointest. Liver. Physiol., 2005, 289: G904-G916).

Figure 6:
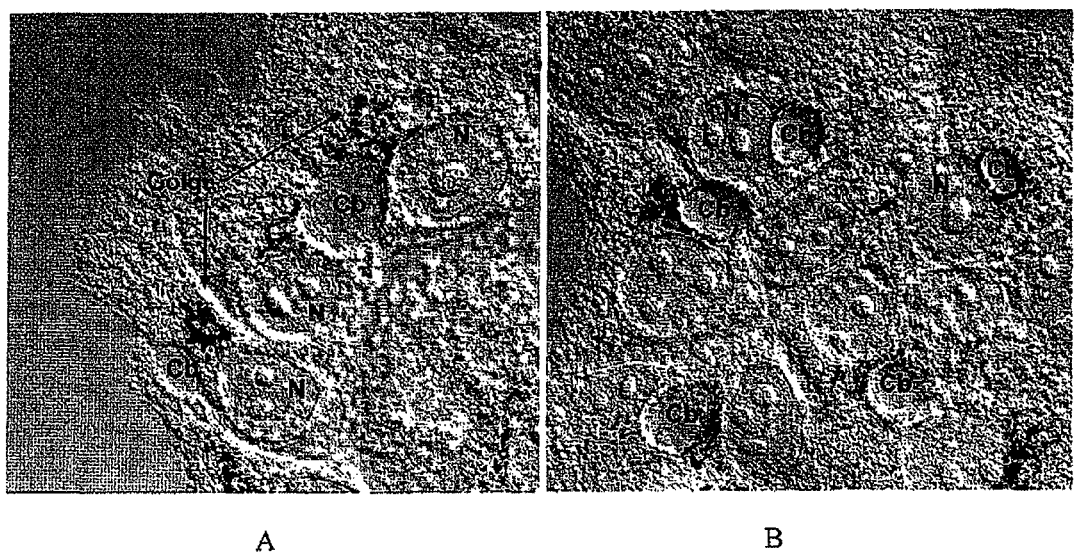
FIG. 6 represents images obtained by fluorescence microscopy (magnification ×63) showing the location of the ATP7B protein in WIF-B9 hepatocytes, under basal conditions (image A) and in the presence of 1 μM of copper Cu(I) (image B)

The location of the ATP7B protein in the WIF-B9 cells is represented in FIG. 6. Under basal conditions (image A), the ATP7B protein is close to the Golgi apparatus, between the bile canaliculus (Cb) and the nucleus (N). After 2 hours of incubation in the presence of 1 µM of copper Cu(I), the ATP7B protein gets closer to the apical membrane, until it surrounds the canaliculi.

The experiments carried out on the WIF-B9 cells also demonstrated that it was possible to see the movement of the ATP7B protein between the basal conditions (copper~0.01 µM) and an excess of copper Cu(I) (1 µM). This movement can therefore be used as a probe for the intracellular concentration of copper Cu(I).

To test the capacity of the compound P³ to reduce the intracellular concentration of copper Cu(I), the cells incubated in an excess of copper Cu(I) are exposed to the compound P³ for at least 2 hours. The incubation with the compound P³ inhibits the movement of the ATP7B protein toward the apical membrane, which demonstrates the absence of an increase in the intracellular concentration of copper Cu(I). The compound P³ is therefore found to be a chelating agent for copper Cu(I) in cellulo.

Figure 7:
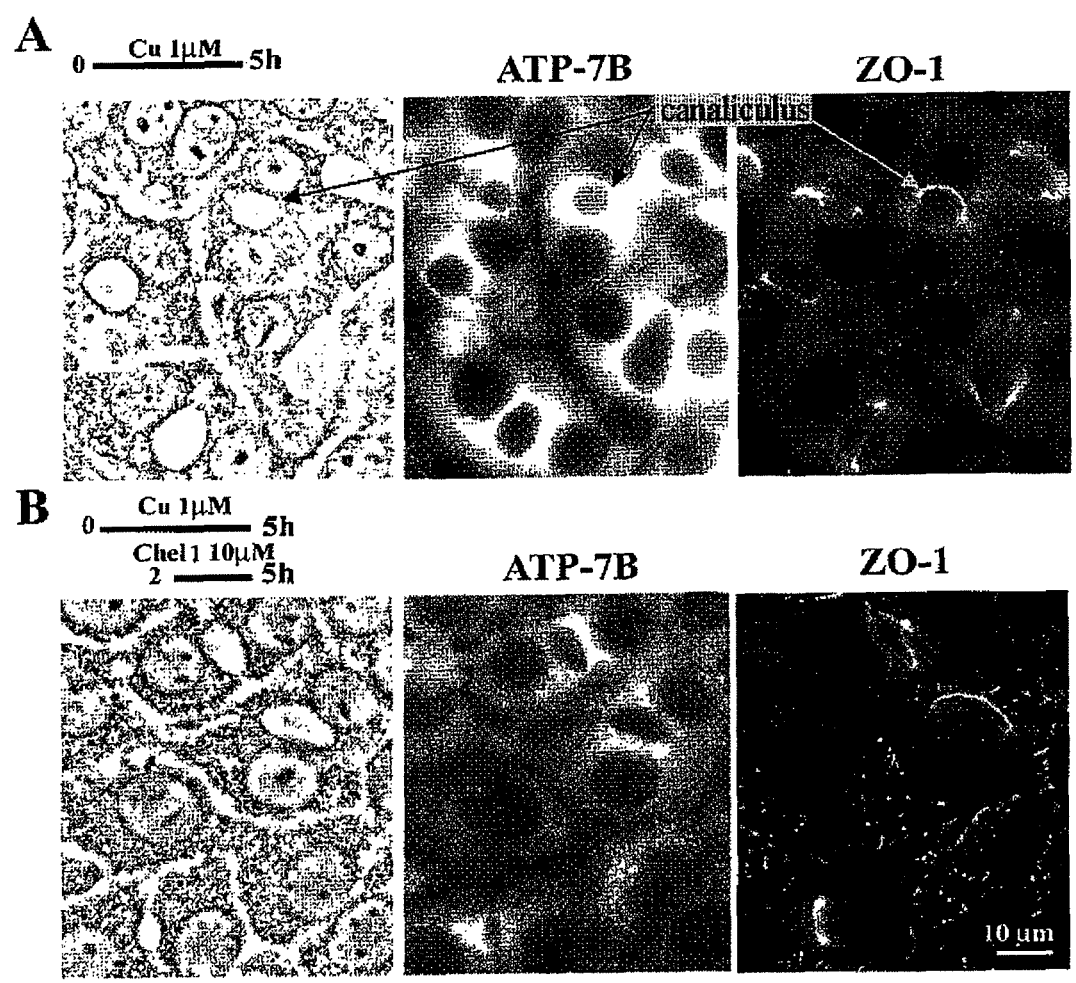
FIG. 7 represents images obtained by fluorescence microscopy (magnification ×63) produced in the presence of 1 μM of copper Cu(I), in the absence of a compound P$^3$ according to the invention (images A) and in the presence of 10 μM of a compound P$^3$ according to the invention (images B).

The position of the ATP7B protein in the presence of 1 µM of copper Cu(I), in the absence (images A) or in the presence (images B) of 10 µM of compound P³ is also represented in FIG. 7 (on the left: image by phase contrast (Nomarski); in the center: fluorescence of the ATP7B protein (visualized by means of the Alexa Fluor 488 antibody); on the right: fluorescence of ZO-1 (protein of the tight junctions or zonula occludens which is visualized by means of the Alexa Fluor 546 antibody; the tight junctions are located at the apex of the hepatocytes and contain numerous proteins, including ZO-1, and they ensure the association of the cells with each other, and therefore the tightness between the inner space of the caniculi and the intercellular medium).

The invention claimed is:
1. A pharmaceutical composition comprising:
at least one cyclodecapeptide compound corresponding to the following formula

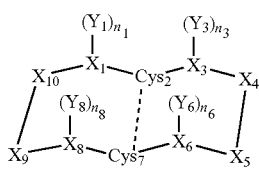

(I):
in which:
the cysteine amino acids $Cys_2$ and $Cys_7$ may or may not be linked by a covalent bond $Cys_2$-$Cys_7$ via their sulfur atoms,
$X_1$, $X_3$, $X_4$, $X_5$, $X_6$, $X_8$, $X_9$ and $X_{10}$, which are identical or different, are amino acids present in their dextrorotary (D) or levorotary form (L),
$n_1$, $n_3$, $n_6$, and $n_8$, which are identical or different, are equal to 0 or 1, and wherein at least one of $n_1$, $n_3$, $n_6$, and $n_8$ must be equal to 1,
$Y_1$, $Y_3$, $Y_6$, and $Y_8$, which are identical or different, represent groups —C(O)—CHNL, —C(O)EL or —NHEL, in which L is a ligand for hepatic or neuronal cells, and E is a spacer arm selected from polyols and optionally substituted alkyl chains having 1 to 12 carbon atoms, and wherein at least one of the groups herein at least one of the groups $Y_1$, $Y_3$, $Y_6$, and $Y_8$ represents a group —C(O)CHNL,
wherein the dipeptide sequences $X_4$-$X_5$ and $X_9$-$X_{10}$, which are identical or different, are chosen from the dipeptides (D)Pro-(L)X or (L)Pro-(D)X', in which X and X' are amino acids, and
at least one pharmaceutically acceptable vehicle,
optionally, one of the amino acids $X_4$, $X_5$, $X_9$, and $X_{10}$, or one of the groups $Y_1$, $Y_3$, $Y_6$, and $Y_8$, may be substituted with a group selected from: —CO-fluorophore, —NH-fluorophore, —C(S)NH-fluorophore, —SO2-fluorophore, =CH-fluorophore and -E'-fluorophore, where E' is a spacer arm selected from phenyl and triazole.

2. The compound as claimed in claim 1, wherein at least one of the amino acids $X_1$, $X_3$, $X_6$, and $X_8$ is a lysine.
3. The compound as claimed in claim 1, wherein X and X' are chosen from glycine, lysine, glutamate or aspartate.
4. The compound as claimed in claim 1, wherein the ligand L for hepatic or neuronal cells is selected from monosaccharides.
5. The compound as claimed in claim 1, wherein the fluorophore is selected from the group consisting of rhodamine, fluorescein, pyronin, coumarin, benzophenone, anthrone, fluorenone, pyridine, quinoleine, acridine, naphthalene, anthracene, naphthacene, pentacene and xanthene.
6. The compound as claimed in claim 1, wherein one of the amino acids $X_4$, $X_5$, $X_9$, and $X_{10}$, or one of the groups $Y_1$, $Y_3$, $Y_6$, and $Y_8$ is substituted with a group selected from the group consisting of —CO-fluorophore, —NH-fluorophore, —C(S)NH-fluorophore, —SO2-fluorophore, =CH-fluorophore, and E'-fluorophore.
7. The compound as claimed in claim 1, wherein at least one of the amino acids $X_1$, $X_3$, $X_6$, and $X_8$ is a lysine bearing a group $Y_1$, $Y_3$, $Y_6$ and $Y_8$.
8. A method for the treatment of Wilson's disease or for the treatment of Alzheimer's disease comprising the step of administering the cyclodecapeptide compound corresponding to the following formula (I) of claim 1 to a patient in need thereof.
9. A method for the diagnosis or treatment of poisoning with metal ions comprising the step of administering the compounds of claim 1 to a patient in need thereof.
10. The method as claimed in claim 9, wherein the patient has been poisoned with copper ions or mercury ions.
11. The method as claimed in claim 9, wherein the metal ion is selected from the group consisting of silver, cadmium, cobalt, copper, mercury, nickel, gold, lead and zinc ions.
12. The compound as claimed in claim 4, wherein the monosaccharide is selected from the group consisting of glucose, galactose and N-acetylgalactosamine.

* * * * *

UNITED STATES PATENT AND TRADEMARK OFFICE
CERTIFICATE OF CORRECTION

PATENT NO. : 9,856,294 B2
APPLICATION NO. : 13/698450
DATED : January 2, 2018
INVENTOR(S) : Delangle et al.

It is certified that error appears in the above-identified patent and that said Letters Patent is hereby corrected as shown below:

In the Claims

Column 25,
Lines 22 and 23, "dextrorotary (D) or levorotary form (L)" should read --dextrorotatory (D) or levorotatory form (L)--;
Line 25, "at least one of $n_t$, $n_3$, $n_6$," should read --at least one of $n_1$, $n_3$, $n_6$,--.

Signed and Sealed this
Nineteenth Day of June, 2018

Andrei Iancu
*Director of the United States Patent and Trademark Office*